US012738370B2

(12) United States Patent
Baumann et al.

(10) Patent No.: US 12,738,370 B2
(45) Date of Patent: Sep. 15, 2026

(54) MEDICAL SOFTWARE FOR DISPLAYING AND ANALYZING BLOOD GLUCOSE DATA FOR USE IN A HETEROGENEOUS COMPUTING NETWORK IN MEDICAL PRACTICES

(71) Applicant: Roche Diabetes Care, Inc., Indianapolis, IN (US)

(72) Inventors: Pascal Baumann, Ulm (DE); Johannes Scheerer, Hannover (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 222 days.

(21) Appl. No.: 18/449,033

(22) Filed: Aug. 14, 2023

(65) Prior Publication Data

US 2023/0386657 A1 Nov. 30, 2023

Related U.S. Application Data

(63) Continuation of application No. PCT/EP2022/054182, filed on Feb. 21, 2022.

(30) Foreign Application Priority Data

Feb. 23, 2021 (EP) .................................... 21158738

(51) Int. Cl.
*G06F 8/65* (2018.01)
*G16H 40/40* (2018.01)
*G16H 40/67* (2018.01)

(52) U.S. Cl.
CPC ............... *G16H 40/40* (2018.01); *G06F 8/65* (2013.01); *G16H 40/67* (2018.01)

(58) Field of Classification Search
CPC ........... G16H 40/40; G16H 40/67; G06F 8/65
See application file for complete search history.

(56) References Cited

U.S. PATENT DOCUMENTS 6,493,871 B1 12/2002 McGuire et al.
9,489,193 B2 11/2016 Reynolds
(Continued)

FOREIGN PATENT DOCUMENTS

AR 066805 A1 9/2009
CN 111459523 A * 7/2020
(Continued)

OTHER PUBLICATIONS

International Preliminary Report on Patentability, PCT/EP2022/054182, Aug. 29, 2023 (10 pages).
(Continued)

*Primary Examiner* — Daxin Wu
(74) *Attorney, Agent, or Firm* — Bose McKinney & Evans LLP

(57) ABSTRACT

A method for updating medical practice software for a plurality of computing devices of a local network, comprising: determining, by a first computing device of the plurality of computing devices, what versions of the medical software are installed on the plurality of computing devices; receiving, at the first computing device, at least one software patch comprising at least one update for a version of the medical software installed on the plurality of computing devices; identifying, by the first computing device, which of the computing devices of the plurality of computing devices has installed thereon a version of the software that requires the software patch; transmitting, by the first computing device, a copy of the software patch to at least one of the computing devices that have been identified; and installing the software patch to update the medical practice software on the at least one computing device.

22 Claims, 2 Drawing Sheets

(56) References Cited

U.S. PATENT DOCUMENTS

| | | | | |
|---|---|---|---|---|
| 10,282,187 | B2 * | 5/2019 | Price | G06F 8/65 |
| 2009/0077549 | A1 * | 3/2009 | Sadja | G06F 8/65 717/178 |
| 2012/0182939 | A1 | 7/2012 | Rajan et al. | |
| 2014/0207844 | A1 * | 7/2014 | Mayo | G06F 8/65 709/203 |
| 2015/0199192 | A1 * | 7/2015 | Borges | A61M 5/14228 717/172 |
| 2017/0286637 | A1 * | 10/2017 | Arrizza | G06F 8/65 |
| 2017/0329969 | A1 * | 11/2017 | Murata | G06F 21/57 |
| 2018/0087910 | A1 * | 3/2018 | Salehi | G01P 15/18 |
| 2019/0102159 | A1 * | 4/2019 | Gur | H04L 67/34 |
| 2021/0157562 | A1 * | 5/2021 | Sethi | G06F 9/453 |
| 2021/0318861 | A1 * | 10/2021 | Ashirvad | G06F 8/61 |

FOREIGN PATENT DOCUMENTS

| | | | | |
|---|---|---|---|---|
| CN | 113032085 | A * | 6/2021 | G06F 8/65 |
| EP | 2 946 290 | B1 | 3/2018 | |
| EP | 2 156 348 | B1 | 8/2018 | |
| JP | 2008-508934 | A | 3/2008 | |
| JP | 2017-146873 | A | 8/2017 | |
| WO | WO 2006/019623 | A2 | 2/2006 | |
| WO | WO 2020/112145 | A1 | 6/2020 | |

OTHER PUBLICATIONS

International Search Report and Written Opinion, PCT/EP2022/054182, Jun. 7, 2022 (13 pages).

* cited by examiner

Figure 1:
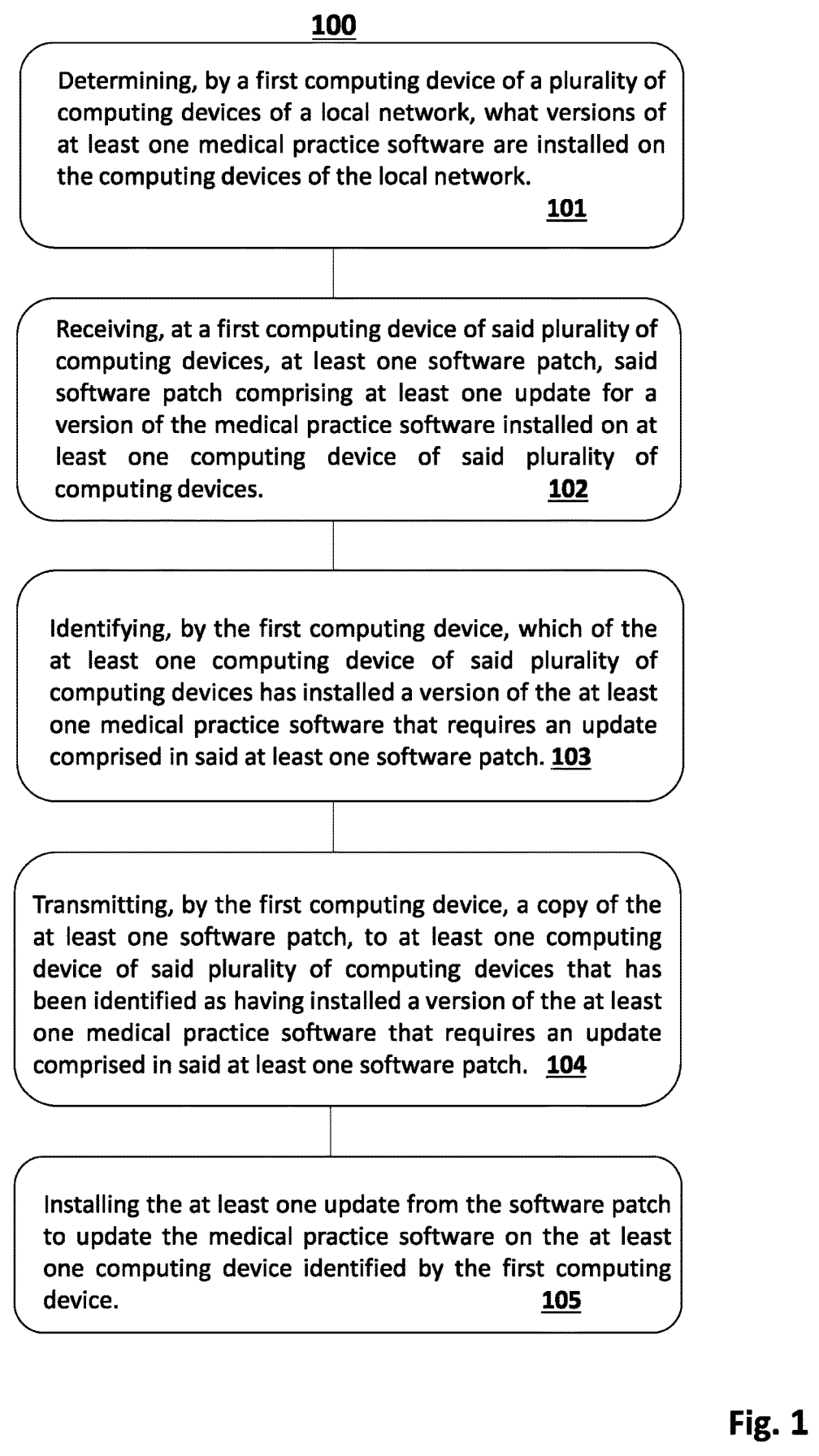

100

Determining, by a first computing device of a plurality of computing devices of a local network, what versions of at least one medical practice software are installed on the computing devices of the local network. 101

Receiving, at a first computing device of said plurality of computing devices, at least one software patch, said software patch comprising at least one update for a version of the medical practice software installed on at least one computing device of said plurality of computing devices. 102

Identifying, by the first computing device, which of the at least one computing device of said plurality of computing devices has installed a version of the at least one medical practice software that requires an update comprised in said at least one software patch. 103

Transmitting, by the first computing device, a copy of the at least one software patch, to at least one computing device of said plurality of computing devices that has been identified as having installed a version of the at least one medical practice software that requires an update comprised in said at least one software patch. 104

Installing the at least one update from the software patch to update the medical practice software on the at least one computing device identified by the first computing device. 105

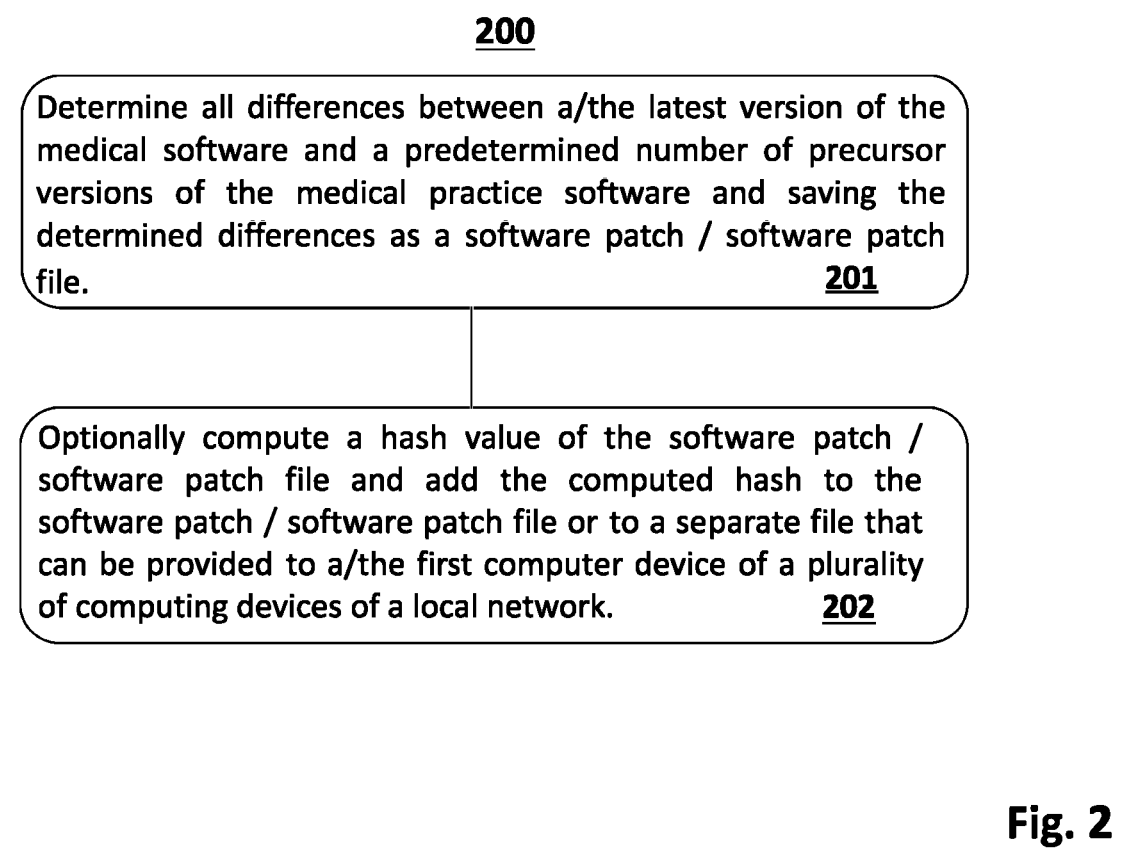

Determine all differences between a/the latest version of the medical software and a predetermined number of precursor versions of the medical practice software and saving the determined differences as a software patch / software patch file. 201

Optionally compute a hash value of the software patch / software patch file and add the computed hash to the software patch / software patch file or to a separate file that can be provided to a/the first computer device of a plurality of computing devices of a local network. 202

Fig. 2

MEDICAL SOFTWARE FOR DISPLAYING AND ANALYZING BLOOD GLUCOSE DATA FOR USE IN A HETEROGENEOUS COMPUTING NETWORK IN MEDICAL PRACTICES

CROSS REFERENCE TO RELATED APPLICATIONS

This is a continuation of PCT/EP2022/054182 filed Feb. 21, 2022, which claims priority to EP 21158738.1 filed Feb. 23, 2021, the entire disclosures of both of which are hereby incorporated herein by reference.

BACKGROUND

This disclosure relates to means for managing, maintaining and updating medical software, in particular medical practice software for displaying and analyzing medical physiological data from medical devices, such as, for example, from medical devices monitoring patient data, e.g. blood glucose data, or from medical devices administering medical drugs, e.g. insulin pumps.

To be able to process medical physiological data from medical devices for diagnosis, therapy and documentation of patients, for example, patients suffering from diabetes, in medical practices or laboratories, dedicated software is required to extract, process, display, analyze, monitor and document the medical data, e.g., the evolution of blood glucose levels.

It is vital that this dedicated medical software is well maintained and regularly updated in order to be able to connect to and extract data from medical devices and to process the data, in particular for all versions of medical devices, i.e. including both legacy versions of medical devices and the most recent device versions.

However, safely maintaining and updating medical practice software is currently a cumbersome and error-prone task that often requires lengthy and intricate user-machine interactions, especially in common heterogeneous computing environments present in medical practices or laboratories, that comprise different computing hardware often running different versions of medical practice software on different operating systems and/or on different operating system versions.

A peer-to-peer software updates scheme is known from EP 2 946 290 B1 wherein an update patch for software is received by one of the peer machines within the network and then the updated version of the software is shared among the peer machines.

U.S. Pat. No. 6,493,871 B1 describes a method and system for downloading software update data for installing a revised software product on a single client computer.

US 2012/0182939 A1 discloses a method and devices providing a wireless communications hub device enabling remote access to electronic medical or fitness devices, wherein updating of the driver software for the medical devices is carried out by a service platform server via the communications hub.

SUMMARY

The present application discloses methods, computing systems and computer-storage media which may be used to facilitate and improve the managing, maintaining and updating of medical practice software, in particular medical practice software for displaying and analyzing medical physiological data from medical devices.

Such methods, computing systems and computer-storage media may also be used to improve the efficiency and robustness with which medical practice software in a heterogeneous distributed local computing network can be maintained and kept up-to-date.

Such methods, computing systems and computer-storage media may also be used to improve the safety and security of medical data processed in computing networks of medical practices or laboratories.

Embodiments disclosed herein include a method for updating at least one medical software, in particular medical practice software for displaying and analyzing medical physiological data, e.g., blood glucose data or other medical data, on at least one computing device of a plurality of computing devices of a local network, e.g., a plurality of computing devices of a local network in a medical practice, may comprise one, some or all of the following exemplary possible steps:

- determining, by a first computing device of said plurality of computing devices, what versions of the at least one medical practice software are installed on the computing devices of said plurality of computing devices;
- receiving, at a first computing device of said plurality of computing devices, at least one software patch, said software patch comprising at least one update for a version of the medical practice software installed on at least one computing device of said plurality of computing devices;
- identifying, by the first computing device, which of the at least one computing device(s) of said plurality of computing devices has installed a version of the at least one medical practice software that requires an update comprised in said at least one software patch;
- transmitting, by the first computing device, a copy of the at least one software patch, to the at least one computing device of said plurality of computing devices that has been identified as having installed a version of the at least one medical practice software that requires an update comprised in said at least one software patch; and
- installing the at least one update from the software patch to update the medical practice software on the at least one computing device identified by the first computing device.

Herein, the exemplary medical physiological data, e.g., blood glucose data, may inter alia originate from medical devices monitoring patient data, e.g., blood glucose data, or from medical devices administering medical drugs, e.g., insulin pumps or similar devices.

Herein, the step of determining, by the first computing device of said plurality of computing devices, what versions of the at least one medical practice software are installed on the computing devices of said plurality of computing devices and/or the step of identifying, by the first computing device, which of the at least one computing device of said plurality of computing devices has installed a version of the at least one medical practice software that requires an update comprised in said at least one software patch, can inter alia be based on querying a local database or local file stored in the local network, e.g., stored on a storage medium of the first computing device. Said local database or local file may store all information regarding what versions of the at least one medical practice software are installed on the computing devices of said plurality of computing devices of the local network and the first computing device may manage and maintain said local database or local file to keep said local database or local file up-to-date.

Herein, a software patch or software patch file can inter alia be understood as a binary patch/executable patch or source code patch for the medical practice software that contains updates and/or changes between older versions of the medical practice software and the most recent version of the medical practice software.

If, for example, the software patch is a source code patch, a compilation of the source code patch to an executable patch can be carried out by the first computing device before a copy of the software patch, i.e., a copy of the executable patch, is transmitted to at least one computing device of said plurality of computing devices, or the source code patch can be compiled on said at least one computing device of said plurality of computing devices and which is not the first computing device after having been transmitted to said at least one computing device by the first computing device.

Furthermore, a software patch can allow the updating of an older or outdated version of the medical practice software to the most recent version without any incremental update steps, i.e., the older version of the medical practice software does not need to be a direct precursor version of the most recent version.

In other words, a software patch can allow a direct update of an older version to the most recent version and skipping any possible other versions of the medical practice software between said older version and the most recent version.

Herein, an update or change to/in the medical practice software can inter alia comprise:

- updating/changing data communication protocols to ensure that the medical practice software can communicate/read data from newer models/versions of medical devices, e.g., new medical devices for monitoring blood glucose levels in patients;
- fixes to bugs/errors in the medical practice software;
- enhanced performance of the medical practice software;
- enhanced functionality of the medical practice software, e.g., new tools or new options to display or analyze or manage medical data; and/or
- updates to user manuals.

Furthermore, a software patch may also be understood herein as a software patch that allows a complete new installation of the medical practice software on a computing device from scratch, i.e., without the computing device having installed thereon any previous version of the medical practice software. Stated differently, the term updating the medical practice software can be inter alia also understood as a complete new/first installation of the medical practice software on a computing device.

The software patch may further be understood as being in the form of a single file.

Herein, the term or the expression of a plurality of computing devices of a local network can be understood as a local network or local area network wherein the said plurality of computing devices/computing systems are physically/geographically close to each other, e.g. said plurality of computing devices are located within the same doctor's office, within the same laboratory or within the same building. However, herein, a plurality of computing devices of a local network can also be understood as comprising networks, wherein the computing devices of a/the plurality of computing devices are distributed across different geographical locations. To ensure safe and confidential communications within such a network distributed over several different geographical locations, e.g., a medical practice or a medical company with branches or offices in different cities or countries, the computing devices may inter alia, for example, be connected via virtual-private-network (vpn) tunnels. Stated differently, the term local network may be generally understood herein as referring to a computing network of the same entity, i.e., the same medical practice or same medical company, regardless of whether the computing devices of said local network are located physically close to each other or not. The exemplary means described herein may therefore provide an improved and more efficient way of updating medical practice software even in cases where the computing devices of the plurality of computing devices of a/the local network are not in the same geographical location.

Furthermore, said exemplary plurality of computing devices of a local network can be a heterogeneous plurality of computing devices, wherein the term heterogeneous plurality of computing devices can be inter alia understood as a plurality of computing devices, wherein the computing devices run different versions of an operating system and/or different versions of the medical practice software and/or have different hardware architectures, e.g., different network connections or different hardware models, or different hardware configurations.

Exemplary computing devices may inter alia comprise personal computers (PCs), such as desktops or laptops or tablets.

The above-identified exemplary computer-implemented method/exemplary method steps for updating at least one medical practice software for displaying and analyzing medical physiological data, e.g., blood glucose data, on at least one computing device of a plurality of computing devices of a local network allows a robust, secure, fast and efficient fully automatic, i.e., without requiring user intervention, mechanism for the updating of a medical practice software in a local network of a heterogeneous plurality of computing devices, such as a plurality of computing devices in a doctor's office, medical practice, medical laboratory or hospital.

Several different software versions can be updated at the same time by using only one software patch. The above and herein exemplary described method allows the updating of different software versions of the medical practice software within a doctor's office.

It is thereby inter alia, for example, also possible that, for a/each given version of the medical practice software, a single individual software patch or a single individual software patch file is provided that enables an update, in particular a direct update, of the given currently installed version to the latest, most recent version of the medical practice software. Said software patch or software patch file may be provided in an archive file format file, e.g., as a ZIP file.

In particular, it is not necessary to install the software new during the update but only the difference between two versions is updated. No sequential update is necessary but, for example, an update from version 3.1 to 3.5 is possible without intermediately installing e.g. versions 3.2, 3.3 and 3.4. Moreover, computers/computing devices to be updated do not need to have an internet connection.

In particular, in the above-described exemplary method steps it is possible that:

- only the first computing device is connected to an external network, e.g. the internet;
- or that none of the computing devices of the local network are connected to an external network, e.g. the internet;

or that only a subset of the plurality of computing devices of the local network has no connection to an external network, e.g. the internet.

Herein, the term external network may be inter alia understood as a network located physically external to the local network of the plurality of computing devices. Said external network may inter alia be a wide area network such as the internet.

The first computing device may inter alia act as a communication hub for the other computing devices of the local network, e.g., the first computing device can be coupled communicatively to all other computing devices of the plurality of computing devices of the local network and the all other computing devices may be coupled to each other by using the first computing device to manage and distribute the communication between the computing devices, i.e., the first computing device may act as communication server for the local network.

Stated differently, the first computing device of the plurality of computing devices of the local network may provide centralized communication services for the local network, wherein the term communication can inter alia be understood as comprising forwarding and/or receiving, and/or exchanging data and/or files and/or commands/instructions between the plurality of computing devices within the local network.

However, it is also possible that all computing devices of the plurality of computing devices of the local network can communicate and exchange data and commands directly with each other.

By avoiding or preventing that any, all, or a majority of the plurality of computing devices of the local network are connected to an external network, bandwidth usage and bandwidth requirements can be optimized and data traffic congestion within the local network can be avoided or reduced.

For example, only the first computing device, which, for example, is acting as the central computing device of the plurality of computing devices of the local network, needs to retrieve or receive the software patch for the medical practice software.

Furthermore, by restricting or completely blocking access of the plurality of computing devices of the local network to any external networks, e.g., the internet, the security and privacy of sensitive medical data can be ensured and improved.

The herein proposed centralized automatic retrieval and distribution mechanism for retrieving/receiving and distributing software patches for medical practice software is faster, easier, safer and more robust than current solutions, in particular, in heterogenic computing environments with a variety of different computer hardware and with computing devices running a variety of different versions of the medical practice software.

For example, the first computing device from the plurality of computing devices of the local network can be connected to a server from an external network, e.g., a web server on the internet.

After the first computing device having determined/identified what versions of the at least one medical practice software are installed on the computing devices of said plurality of computing devices, the first computing device may query said server from the external network, e.g., a web server on the internet, to check whether there are any new software patches available for at least one computing device of said plurality of computing devices of the local network.

Said querying of the server from the external network by the first computing device may comprise downloading/retrieving, by the first computing device, from said external server a file that comprises information on which software patches are available for which versions of said at least one medical practice software.

After, for example, having determined, by the first computing device that software patches with updates for software versions currently installed on the plurality of computing devices of the local network are available, the first computing device may then download said software patch(es).

Said determination can inter alia be based on comparing the information, e.g., metadata, in the file retrieved from the server of the external network with the information comprised in the local database or in the local file stored in the local network that may store all information regarding what versions of the at least one medical practice software are installed on the computing devices of the local network.

Furthermore, in order to facilitate the download, the first computing device may, for example, again make use of said exemplary file provided by the external server and which comprises information on which software patches are available for which versions of said at least one medical practice software, and which, in addition, may also comprise download links for specifying a location, e.g., a directory/Uniform Resource Locator (URL) or web address, from which the software patch(es) can be downloaded.

In other words, the step of receiving, at the first computing device of said plurality of computing devices, the at least one software patch, can comprise downloading the at least one software patch from the server external to the local network, wherein the downloading of the at least one medical practice software patch can be based on utilizing a server download link provided in the file from the external server that was downloaded by the first computing device.

It is to be noted that the above-described exemplary steps of query and/or download/retrieval by the first computing device of the file from the external server, wherein the file comprises information on which software patches are available for which versions of said at least one medical practice software, are entirely optional.

The first computing device may, for example, be configured such that it automatically at regular, irregular or predetermined times/time intervals, e.g., once a day, once a week, checks for the presence of software patches at a predetermined location, e.g., a directory/Uniform Resource Locator (URL) or web address, on an external server and if software patches are present on said external server, downloads said software patches in any case, even without first checking for which versions of the software the software patches are intended for.

In this exemplary scenario, the first computing device, may, for example, then check the software patch(es) only after download of the software patch(es) to determine whether the software patch(es) are suited for any software version(s) currently installed on at least one of the computing devices of the local network.

This exemplary determination may, for example, be carried out by comparing information, e.g., metadata, comprised in the downloaded software patch(es) or comprised in separate accompanying files, with the information comprised in the above-mentioned exemplary local database or local file that may have stored all information regarding what versions of the at least one medical practice software are installed on the computing devices of said plurality of computing devices of the local network.

However, it is also possible that the determination of whether any software patch(es) that might be present on the external server are suited for updating the versions of the at least one medical practice software currently installed on the computing devices of the local network or not, can be carried out prior to the download/retrieval of the actual software patch(es) from the external server, by the first computing device.

For example, as indicated previously, the first computing device may first download/retrieve a file from the external server, wherein the file comprises information on which software patches are available for which versions of said at least one medical practice software and then compare the retrieved information with the information comprised in the above-mentioned exemplary local database or local file in order to determine whether to download/retrieve any software patch(es) present on/provided by the external server. This advantageously ensures that only software patch(es) that are useful/required/necessary for updating the computing devices of the local network are retrieved by the first computing device.

The above exemplary described steps of a computer-implementable mechanism and method allow a fully automatic update of medical software, e.g. medical practice software, for displaying and analyzing blood glucose data on at least one computing device of a plurality of computing devices of a local network, in particular, in a heterogeneous environment of computing devices, via utilization of an external server and without the need for any human/user interaction with the computing devices of said local network, in particular without any need for interacting with the versions of the medical practice software installed on the computing devices of said local network.

However, it is also possible that in addition to or alternatively to, for example, the step of receiving, at the first computing device of said plurality of computing devices, the at least one software patch, may comprise loading/retrieving the software patch from a physical computer-storage media, in particular from a physical external computer-storage media, in particular an external non-volatile storage media or memory, e.g., a hard drive or memory stick, e.g., a USB (universal series bus) stick, or a digital optical disc data storage, connected to the first computing device.

In this exemplary scenario, neither the first computing device nor other computing devices of said local network, need to be connected to an external network, e.g., the internet. This can further improve the security, privacy and safety of any medical data processed by the local network.

Herein the step of providing the software patch(es) to the first computing device, which then can distribute the received software patch(es) to the other computing devices of the local network, may require some human interaction, e.g., connecting an external computer-storage media to the first computing device, thereby providing a semi-automatic mechanism and method for the updating of medical practice software.

However, even this exemplary semi-automatic mechanism and method for the updating of medical practice software is still faster and more efficient than current mechanisms, in particular, in cases when the computing environment of the local network and/or the versions of the medical practice software installed on the computing devices of the local network are heterogeneous.

Herein, in the exemplary described mechanism and method for the updating of medical practice software, the first computing device may, for example, determine that on at least two computing devices of the local network, different versions of the software are installed that require an update and further determine that retrieved/retrievable software patch(es) comprises/comprise updates for said different versions of the medical practice software.

Said determination by the first computing device may inter alia be based on comparing information comprised in the local database or in the local file stored in the local network and that may store all information regarding what versions of the at least one medical practice software are installed on the computing devices of the local network with information on the available software patch(es), wherein the information on the available software patch(es) may inter alia originate from the above-mentioned file provided by/retrieved from a server external to the local network or from an external computer storage media, and which comprises information on which software patches are available for which versions of said at least one medical practice software, or wherein the information on the available software patch(es) is extracted from information, e.g. metadata, comprised in a received software patch.

To further facilitate the safety, security and robustness of the herein described exemplary mechanism and method for the updating of medical practice software, the first computing device may be configured for verifying the integrity and validity of the received software patch(es) using a hash algorithm.

For example, after retrieving the software patch(es), by the first computing device, the first computing device may compute a hash value of a cryptographic hash function and compare the computed hash value with a reference hash value, wherein the reference hash value may, for example, be provided from a server external to the local network, e.g., the reference hash value may be comprised in the above-mentioned file provided by/retrieved from a server external to the local network.

After a successful and optionally verified retrieval of the software patch(es), by the first computing device, the first computing device may update locally saved information on the local availability of software patches for the computing devices of the local network.

The exemplary step of identifying, by the first computing device, which of the at least one computing device(s) of said plurality of computing devices has installed a version of the at least one medical practice software that requires an update comprised in said at least one software patch can, as previously indicated, for example, be based on comparing the information, e.g., metadata, in a/the file retrieved from the server of the external network and/or on information extracted from a retrieved software patch with the information comprised in the local database or in the local file stored in the local network that may store all information regarding what versions of the at least one medical practice software are installed on the computing devices of the local network.

Furthermore, said exemplary step of identifying the computing device(s) that are to be updated may also take into account the possibility of recognizing or determining that some/a particular computing device cannot perform an update or is not compatible with an update.

For example, it could be that the hardware configuration or operating system configuration of a particular computing device from the local network is not capable of processing or executing the update, i.e., is not capable of running an updated version of the medical practice software.

For example, a particular computing device may not have enough memory space or its operating system may not be compatible with a newer updated version of the medical practice software. Such a computing device that may not be compatible with the retrieved software patches may be marked, by the first computing device, as problematic in the local database or in the local file stored in the local network that may store all information regarding what versions of the at least one medical practice software are installed on the computing devices of the local network.

For example, the first computing device may set a problem flag, e.g., an integer flag, in the local database or in a local file. A computing device may also be declared manually by a user as a problematic computing device, i.e., for example, a user can manually set the exemplary problem flag in the local database or in the local file.

The first computing device can then, for example, optionally take this information on problematic computing devices of the local network into account and can, for example, avoid transmitting a copy of the retrieved software patch(es) to the problematic computing devices (or avoid making a copy of the retrieved software patch(es) available to the problematic computing devices), thereby increasing the chances for an error-free and conflict-free installation of the retrieved software patch(es) across the plurality of computing devices of the local network.

However, the avoidance of transmitting a copy of the retrieved software patch(es) to computing devices declared as problematic is optional and the first computing device can also transmit a copy of the at least one software patch to the at least one computing device of said plurality of computing devices that has been identified as having installed a version of the at least one medical practice software that requires an update comprised in said at least one software patch, regardless of whether the identified computing device is marked as problematic, i.e., regardless of whether the identified computing device may be able to support the updated version of the medical practice software or not.

The exemplary step of transmitting, by the first computing device, a copy of the at least one software patch, to at least one computing device of said plurality of computing devices that has been identified as having installed a version of the at least one medical practice software that requires an update comprised in said at least one software patch, may also be understood as a step of the first computing device making available a copy of the at least one software patch for retrieval by at least one computing device of said plurality of computing devices via the local network.

After a copy of the at least one software patch has been received by a computing device, either due to a transmission from the first computing device or due to the computing device having retrieved/downloaded a copy of the at least one software patch from the first computing device, an installation of the software patch, i.e., an installation of at least one update from the software patch to update the software on the at least one computing device identified by the first computing device can be carried out. If need be, the at least one software patch may be unpacked by the computing device before the installation begins.

Said installation of the at least one update from the software patch to update the medical practice software on the at least one computing device of the local network identified by the first computing device can, for example, be carried out in at least one of the following ways:

- fully automatic installation, e.g., initiated by/triggered by/in response to a command from the first computing device transmitted to the at least one identified computing device, or based on a command/flag or instructions comprised in a/the file or the software patch retrieved from an external server, or triggered/initiated by an automatic check of the medical practice software during start of the medical practice software that checks whether any software patch/update is locally available, e.g., available/provided by the first computing device, or triggered/initiated by a system boot/restart of the identified computing device, wherein, for example, an autostart configuration of the identified computing device has a link/an entry to carry out the installation during a start of the operating system of the computing device if a software patch is locally available;
- manual installation, e.g., a user can manually initiate the installation, e.g., by executing a script or otherwise initiating a guided installation with a graphical user interface.

It is to be noted that the decision of whether a fully automatic or a manual installation is performed can inter alia, for example, be fully controlled remotely by an external server, by providing all information on required parameters and/or settings and/or configurations to the first computing device, which can save and store said information in the previously mentioned local database or local file.

In the case of a fully automatic installation, there is no need for manually carrying out any configuration changes on the side of an/the identified computing device to start the installation process of a software patch.

It is further noted that the installation of the software patch, i.e., the installation of the at least one update from the software patch to update the medical practice software on the at least one computing device identified by the first computing device, can be carried out as a background process on the computing device, in case there is no version of the medical practice software currently running on the computing device.

In case a version of the medical practice software is currently running on the computing device, the user can be notified that the running instance of the medical practice software will be terminated and that an update will be installed and the software will be restarted.

Regardless of whether an instance of the medical practice software is running on an identified computing device, the above-described steps for retrieving and distributing and/or unpacking the software patch(es) can be carried out as background processes without interrupting any possible running instances of the medical practice software.

After an installation of the at least one update from the software patch to update the software on the at least one computing device of the local network has been carried out, the validity and success of the update can be checked by, for example, using a further hash algorithm.

For example, after the installation, the computing device may compute/evaluate a hash value that can be compared with a hash reference value that was provided with the software patch.

This optional hash algorithm mechanism can be performed in addition to the optional hash algorithm mechanism that can be used for verifying the integrity and validity of the received software patch. For this purpose, the software patch may comprise at least two different hash reference values; one to check the integrity and validity of the software patch after download by the first computing device and another one to check the success of the update installation.

In case it is determined from the exemplary hash value evaluation that the installation was not successful, it is, for example, possible that the medical practice software can be reset to the previously installed version using a backup that, for example, was made before the start of the installation of the software patch. In general, it is possible that, if a backup is available, the medical practice software can be reset/reverted to a previous version, e.g., a backed-up version, in case the update installation fails.

For completeness, it is noted that the creation of a software patch/of software patches comprising at least one update for the medical practice software, provided for the retrieval by the first computing device, can also be fully automatic.

For example, a possible packaging or patch creation process on the above-mentioned server external to the local network can create software patches for an arbitrary number/any number of precursor versions of the latest version of the medical practice software, for example, by determining any/all differences between the latest version of the medical practice software and any number of older precursor versions, e.g., the last five precursor versions, of the medical practice software and writing the determined differences into a software patch or saving the determined differences as a software patch/as a plurality of software patches.

If need be, a plurality of software patches can, for example, be also bundled into a single file, e.g., an archive file format file, e.g. a ZIP file.

Any information, e.g., metadata, on the created patch, e.g., information on versions of the medical practice software or hash values for checking the validity of the patch and/or hash values for checking whether a patch has been successfully installed, can, for example, be included in the created patch itself and/or can be provided in a separate file, such as in the previously mentioned file provided by the external server.

Furthermore, any instructions or functions that might be needed for the installation of the software patch might be also included in the software patch, for example, in form of a script.

In any case, the created software patch or created software patches and/or created information file(s) and/or scripts may be provided as a single file/bundled into a single file for retrieval by the first computing device.

Furthermore, as previously indicated, it is also possible that a software patch also comprises a complete version of the medical practice software for installing a version of the medical practice software on a computing device from scratch.

Furthermore, it is conceivable that the above described exemplary patch creation process creates a software patch/software patches that are already tailored to the needs and requirements of specific medical practices, thereby further improving the efficiency of the distribution and update mechanism, as it can be ensured that only patches relevant for a specific medical practice are provided for and retrieved by a/the first computing device of a specific medical practice.

The above and in the following described means for distributing, maintaining and installing updates for medical practice software, in particular for medical practice software for displaying and analyzing blood glucose data on at least one computing device of a plurality of computing devices of a local network, provides an efficient, secure and robust semi-automatic or fully-automatic way for keeping medical software in medical practices up-to-date and to ensure that medical data from all versions of medical devices, including the most recent models of medical devices, can be safely processed, visualized and analyzed.

The above and in the following described computer-implementable method steps may, for example, be carried out by a computing system or computing device, e.g., a computing device of a plurality of computing devices of a local network, comprising:

- one or more processors, e.g. central processing units;
- one or more computer-readable storage media comprising computer-executable instructions which, when executed by the one or more processors, cause the one or more processors to perform a method according to one, some or all of the above and in the following exemplary described method steps for updating the at least one medical practice software on at least one computing device of a/the plurality of computing devices of a/the local network.

Furthermore, the above and in the following described computer-implementable method steps may be stored on one or more computer-storage media, e.g., non-volatile computer-storage media, storing computer-executable instructions that, when executed by a computer system, perform a method according to either one, some or all of the above and in the following exemplary described method steps for updating the at least one medical practice software on the at least one computing device of a/the plurality of computing devices of a/the local network.

BRIEF DESCRIPTION OF THE DRAWINGS

The above mentioned and other features of this disclosure, and the manner of attaining them, will become more apparent and the disclosure itself will be better understood by reference to the following description of embodiments taken in conjunction with the accompanying drawings, wherein:

FIG. 1 is an exemplary flow diagram for the retrieval, distribution and installation of software patches for a medical practice software.

FIG. 2 is an exemplary flow diagram for the creation of a software patch.

Corresponding reference characters indicate corresponding parts throughout the several views. Although the exemplification set out herein illustrates embodiments of the invention, in several forms, the embodiments disclosed herein are not intended to be exhaustive or to be construed as limiting the scope of the invention to the precise forms disclosed.

DETAILED DESCRIPTION

FIG. 1 schematically shows exemplary possible steps of a computer-implementable method 100 for updating at least one medical practice software for displaying and analyzing blood glucose data on at least one computing device of a plurality of computing devices of a local network.

A first computer of the plurality of computing devices may first determine 100 what versions of the at least one medical practice software are installed on the computing devices of the plurality of computing devices of the local network.

This step 100 may inter alia comprise querying a local database or local file stored in the local network, e.g., stored on a storage medium of the first computing device. The local database or local file may store all information regarding what versions of the at least one medical practice software are installed on the computing devices of the plurality of computing devices of the local network and the first computing device may manage and maintain the local database or local file to keep the local database or local file up-to-date, i.e., the first computing device may record and track any changes made to the versions of the medical practice software currently installed on the computing devices of the plurality of computing devices of the local network.

In an exemplary second step, the first computing device of the plurality of computing devices may receive 102 at least one software patch/software patch file, wherein the software patch can comprise at least one update for a version of the medical practice software installed on the at least one computing device of the plurality of computing devices.

As exemplary described further above, the first computing device may receive or retrieve the at least one software patch from a server external to the local network, e.g., from a web server.

Furthermore, it is possible that, prior to receiving or retrieving the at least one software patch from the external server, the first computing device may have queried the server from the external network to check whether there are any new software patches available for the at least one computing device of the plurality of computing devices.

This querying of the external server may, for example, inter alia comprise downloading, by the first computing device, from the external server a file that comprises information on/about which software patches are available for which versions of the at least one medical practice software.

This exemplary file describing the available software patches can for example be provided by and maintained by the external server. In addition, the file provided by the external server may, for example, inter alia comprise download links that specify from where the software patches can be downloaded.

After the first computing device has received or retrieved the at least one software patch, the first computing device may identify 103 which of the at least one computing device of the plurality of computing devices has installed a version of the at least one medical practice software that requires an update comprised in the received or retrieved at least one software patch.

The identification of the computing devices requiring/being eligible for the update comprised in the at least one software patch may be based on comparing the information, e.g., metadata, from the file retrieved from the server of the external network and/or on information extracted from a retrieved software patch with the information comprised in the local database or in the local file stored in the local network.

After having identified the computing devices to which the at least one software patch should/can be applied, the first computing device may transmit 104 a copy of the at least one software patch to at least one computing device of the plurality of computing devices that has been identified as having installed a version of the at least one medical practice software that requires an update comprised in the at least one software patch.

As has been indicated further above, the step of transmitting 104 a copy of the at least one software patch to the at least one computing device of the plurality of computing devices can also be understood as comprising the case/possibility that the at least one computing device itself retrieves/downloads a copy of the at least one software patch from the first computing device acting as a server for the local network. This retrieval might, for example, be in response to a notification from the first computing device or in response to an automatic query of the least one computing device checking for the possible availability of a software patch on the first computing device, e.g., on a local network drive provided by the first computing device.

Finally, the at least one update from the software patch to update the medical practice software on the at least one computing device identified by the first computing device can be installed 105.

For completeness, it is noted that the installation of the software patch to update the medical practice software on the at least one computing device, when possible, can preserve/maintain any previous specific configurations of the currently installed version of the medical practice software.

In other words any specific configurations of the medical practice software that, for example, were made to adapt/configure the medical practice software to specific requirements of an individual medical practice can be maintained/carried over, so that the user of the updated version does not need to reconfigure tools or functions again that he already had configured. However, if the update provides new tools or new functionalities, the new tools or new functionalities can be provided with default settings and the user can be notified about the new tools/new functions and new configuration settings.

As has been indicated further above, all steps 101, 102, 103, 104 and 105 can be carried out fully automatically, i.e., without any intervention by a human user.

FIG. 2 schematically shows exemplary possible steps for/during creation 200 of a software patch/software patches for a medical practice software.

These steps may be carried out by a server, e.g. a web server, external to a local network formed by a plurality of computing devices onto which a software patch is to be applied for updating a version/versions of medical practice software currently installed on the plurality of computing devices of the local network.

Furthermore, these steps can be carried out prior to the exemplary described steps for the retrieval, distribution and installation of software patches for a medical practice software depicted in FIG. 1.

An exemplary software patch for a medical practice software can, for example, be created/generated by determining 201 all differences between the latest version of the medical practice software and a predetermined number of precursor versions of the medical practice software and saving the determined differences as a software patch/software patch file.

To improve the safety and robustness during distribution and installation/application of the created software patch, it is optionally possible to compute 202 a hash value of the software patch/software patch file and add the computed hash to the software patch/software patch file or to a separate file that can be provided to the first computer device of a plurality of computing devices of the local network.

While this invention has been described as having an exemplary design, the present invention may be further modified within the spirit and scope of this disclosure. This application is therefore intended to cover any variations, uses, or adaptations of the invention using its general principles.

What is claimed is:

1. A method for updating medical practice software for displaying and analyzing blood glucose data or other medical data on a computing device of a plurality of computing devices of a local network, the method comprising:

determining, by a first computing device of the plurality of computing devices, what versions of the medical practice software are installed on the computing devices of the plurality of computing devices;

receiving, at the first computing device of the plurality of computing devices, at least one software patch comprising at least one update for a version of the medical practice software installed on one or more computing devices of the plurality of computing devices;

identifying, by the first computing device, which of the plurality of computing devices has installed thereon the version of the medical practice software that requires the at least one update provided by the at least one software patch;

transmitting, by the first computing device, a copy of the at least one software patch, to at least one computing device of the plurality of computing devices that has been identified as having, installed thereon, the version of the medical practice software that requires the at least one update provided by the at least one software patch;

installing the at least one update from the at least one software patch to update the medical practice software on the at least one computing device;

wherein it is determined, by the first computing device, that on at least two computing devices of the plurality of computing devices, different versions of the medical practice software are installed that require an update, wherein the at least one software patch comprises updates for the different versions of the medical practice software to update the medical practice software to a most recent version and wherein one of the different versions of the medical practice software is not a direct precursor version of the most recent version; and wherein configuration settings of the medical practice software on the at least two computing devices are preserved during the installation of the at least one update.

2. The method according to claim 1, wherein only the first computing device is connected to an external network; or wherein none of the computing devices of the local network are connected to an external network; or wherein a subset of the plurality of computing devices of the local network has no connection to an external network.

3. The method according to claim 1, wherein the first computing device is connected to a server from an external network and wherein after the first computing device has determined what versions of the medical practice software are installed on the computing devices of said plurality of computing devices:

querying, by the first computing device, the server from the external network to check whether there are any new software patches available for the computing devices of the plurality of computing devices, the querying comprising downloading, by the first computing device, from the server a file that comprises information on which software patches are available for which versions of the medical practice software; and wherein the step of receiving, at the first computing device of the plurality of computing devices, the at least one software patch, comprises downloading the at least one software patch from the server external to the local network.

4. The method according to claim 1, wherein the step of receiving, at the first computing device of said plurality of computing devices, the at least one software patch, comprises loading the software patch from a physical external computer-storage media connected to the first computing device.

5. A method for updating medical practice software for displaying and analyzing blood glucose data or other medical data on a computing device of a plurality of computing devices of a local network, the method comprising:

determining, by a first computing device of the plurality of computing devices, what versions of the medical practice software are installed on the computing devices of the plurality of computing devices;

receiving, at the first computing device of the plurality of computing devices, at least one software patch comprising at least one update for a version of the medical practice software installed on one or more computing devices of the plurality of computing devices;

identifying, by the first computing device, which of the plurality of computing devices has installed thereon the version of the medical practice software that requires the at least one update provided by the at least one software patch;

transmitting, by the first computing device, a copy of the at least one software patch, to at least one computing device of the plurality of computing devices that has been identified as having, installed thereon, the version of the medical practice software that requires the at least one update provided by the at least one software patch;

installing the at least one update from the at least one software patch to update the medical practice software on the at least one computing device; and wherein the at least one software patch comprises at least one update for a version of the medical practice software that is created in a fully automatic process and wherein the at least one software patch is created by determining all differences between a latest version of the medical practice software and a predetermined number of precursor versions of the medical practice software and saving the determined differences as a software patch.

6. The method according to claim 1, wherein the first computing device verifies the integrity and validity of the received at least one software patch using a hash algorithm.

7. The method according to claim 1, wherein the first computing device communicatively couples the computing devices of the plurality of computing devices to each other to exchange data, files and/or instructions between the plurality of computing devices.

8. The method according to claim 1, wherein the at least one software patch comprises at least one update for a version of the medical practice software that is created in a fully automatic process.

9. The method according to claim 1, wherein the step of identifying, by the first computing device, which of the plurality of computing devices has installed thereon the version of the medical practice software that requires the at least one update, comprises determining that a computing device of the plurality of computing devices cannot perform or is not compatible with an update in the software patch.

10. The method according to claim 1, wherein, before installing the at least one update from the software patch to update the medical practice software on the at least one computing device, a backup of the current version of the medical practice software installed on the at least one computing device is made.

11. The method according to claim 1, wherein, after installing the at least one update from the software patch to update the medical practice software on the at least one computing device, the success and validity of the installation is checked using a hash algorithm.

12. The method according to claim 1, wherein installing the at least one update from the software patch to update the medical practice software on the at least one computing device is initiated in response to an instruction from a server from an external network.

13. A computing system comprising:

one or more processors; and one or more computer-readable storage media comprising non-volatile computer-executable instructions which, when executed by the one or more processors, cause the one or more processors to perform the method according to claim 1 for updating the medical practice software on the at least one computing device.

14. One or more computer-storage media storing computer-executable instructions that, when executed by a computer system, perform the method according to claim 1 for updating the medical practice software on the at least one computing device.

15. The method according to claim 1, wherein the first computing device is connected to a server from an external network and wherein after the first computing device has determined what versions of the medical practice software are installed on the computing devices of said plurality of computing devices:

querying, by the first computing device, the server from the external network to check whether there are any new software patches available for the computing devices of the plurality of computing devices, the querying comprising downloading, by the first computing device, from the server a file that comprises information on which software patches are available for which versions of the medical practice software; and wherein the step of receiving, at the first computing device of the plurality of computing devices, the at least one software patch, comprises downloading the at least one software patch from the server external to the local network, and wherein downloading of the at least one software patch comprises using a server download link provided in the file downloaded by the first computing device.

16. The method according to claim 1, wherein the step of identifying, by the first computing device, which of the plurality of computing devices has installed thereon the version of the medical practice software that requires the at least one update, comprises determining that a problematic computing device of the plurality of computing devices cannot perform or is not compatible with an update in the software patch and the copy of the at least one software patch is not transmitted to the problematic computing device.

17. The method according to claim 1, wherein the first computing device and each of the other computing devices in the plurality of computing devices has a version of the medical practice software installed thereon and is adapted to run the medical practice software.

18. The method according to claim 1, wherein the plurality of computing devices are all personal computers and are one of a desktop computer, a laptop computer or a tablet computer.

19. The method according to claim 5, wherein it is determined, by the first computing device, that on at least two computing devices of the plurality of computing devices, different versions of the medical practice software are installed that require an update and wherein the at least one software patch comprises updates for the different versions of the medical practice software.

20. The method according to claim 5, wherein the step of receiving, at the first computing device of said plurality of computing devices, the at least one software patch, comprises loading the software patch from a physical external computer-storage media connected to the first computing device wherein the physical external computer-storage media is selected from the consisting of a hard drive, a memory stick and a digital optical disc data storage.

21. The method according to claim 5, wherein the predetermined number of precursor versions is greater than one.

22. The method according to claim 20, wherein none of the plurality of computing devices are connected to an external network.

* * * * *